United States Patent [19]

Nelson

[11] 4,011,257

[45] Mar. 8, 1977

[54] PROCESS FOR PREPARING 5-OXA PROSTAGLANDIN ANALOGS

[75] Inventor: Norman A. Nelson, Galesburg, Mich.

[73] Assignee: The Upjohn Company, Kalamazoo, Mich.

[22] Filed: Feb. 26, 1976

[21] Appl. No.: 661,573

Related U.S. Application Data

[60] Continuation of Ser. No. 524,481, Nov. 18, 1974, abandoned, which is a division of Ser. No. 361,990, May 21, 1973, Pat. No. 3,864,387.

[52] U.S. Cl. .......................................... 260/473 G
[51] Int. Cl.$^2$ ........................................ C07C 69/76
[58] Field of Search ............................... 260/473 G

[56] References Cited

UNITED STATES PATENTS 3,873,607  3/1975  Bernady et al. ............... 260/514 D Primary Examiner—Paul J. Killos
Attorney, Agent, or Firm—Morris L. Nielsen

[57] ABSTRACT

Process for preparing 5-oxa phenyl- and phenoxy-substituted prostaglandin-type compounds. These compounds are useful for a variety of pharmacological purposes, including anti-ulcer, inhibition of platelet aggregation, increase of nasal patency, labor inducement at term, and wound healing.

12 Claims, No Drawings

PROCESS FOR PREPARING 5-OXA PROSTAGLANDIN ANALOGS

This application is a continuation of my co-pending application Ser. No. 524,481 filed Nov. 18, 1974, now abandoned, which was a division of my co-pending application Ser. No. 361,990, filed May 21, 1973, now issued as U.S. Pat. No. 3,864,387.

BACKGROUND OF THE INVENTION

This invention relates to novel compositions of matter, to novel methods for producing those, and to novel chemical intermediates useful in those processes. Particularly, this invention relates to certain novel analogs of prostaglandins $E_1$, $F_{1\alpha}$, $F_{1\beta}$, $A_1$, and $B_1$ in which the C-5 methylene ($-CH_2$) in the prostanoic acid structure is replaced by oxygen ($-O-$).

The essential material for this application, including the background of the invention, the disclosure of the invention, and the description of the preferred embodiments, including Preparations and Examples, is incorporated by reference from U.S. Pat. No. 3,864,387, columns 1–89 inclusive, under the provisions of M.P.E.P. 608.01(p).

SUMMARY OF THE INVENTION

It is a purpose of this invention to provide novel 5-oxa prostagalandin E, F, A, and B analogs. It is a further purpose to provide novel 5-oxa prostaglandin analogs with a variety of substituents and degrees of saturation in the side chains. It is a further purpose to provide 5-oxa prostaglandin analogs having the 11-deoxy ring-structure in which the 11-hydroxy is replaced by hydrogen. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The novel prostaglandin analogs of this invention each have an oxygen ($-O-$) in place of the methylene ($-CH_2-$) moiety at the 5-position of the prostanoic acid formula. They are represented by the generic formula

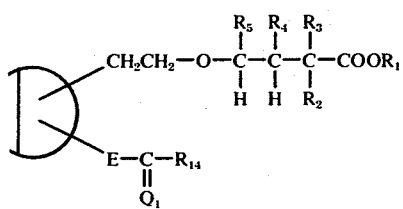   VII wherein D is one of the six carbocyclic moieties:

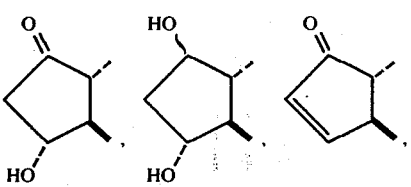

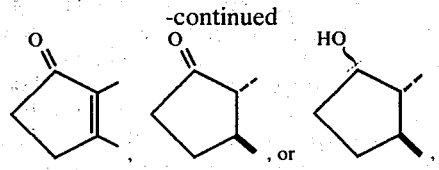

wherein ~ indicates alpha or beta attachment of hydroxyl to the cyclopentane ring; wherein E is $-CH_2CH_2-$ or

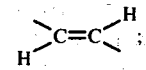

wherein $Q_1$ is

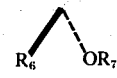

or

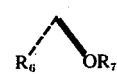

wherein $R_6$ and $R_7$ are hyrogen or alkyl of one to 4 carbon atoms, inclusive, being the same or different; wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different with the proviso that no more than one of $R_3$, $R_4$, and $R_5$ is alkyl; and wherein $R_{14}$ is

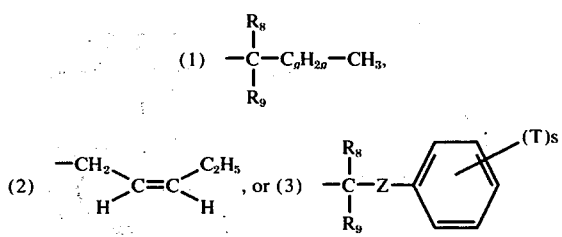

with the proviso that $R_{14}$ is

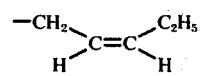

only when E is

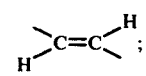

wherein $C_gH_{2g}$ is alkylene of one to 9 carbon atoms, inclusive, with one to 5 carbon atoms, inclusive, in the chain between $-CR_8R_9-$ terminal methyl; wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro; wherein T is alkyl of one to 4 carbon atoms, inclusive, fluoro, chloro, trifluoromethyl, or —$OR_{10}$, wherein $R_{10}$ is hydrogen or alkyl of 1 to 4 carbon atoms, inclusive, and s is zero, one, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive, between —$CR_8R_9$— and the ring.

The presently described acids and esters of the 5-oxa prostaglandin analogs include compounds of the following formulas which are intended to represent the same optically form as of the naturally occurring prostaglandins. There are also included the racemic compounds represented by each respective formula and the mirror image thereof. There are also included the alkanoates of two to 8 carbon atoms, inclusive and also the pharmacologically acceptable salts thereof when $R_1$ is hydrogen.

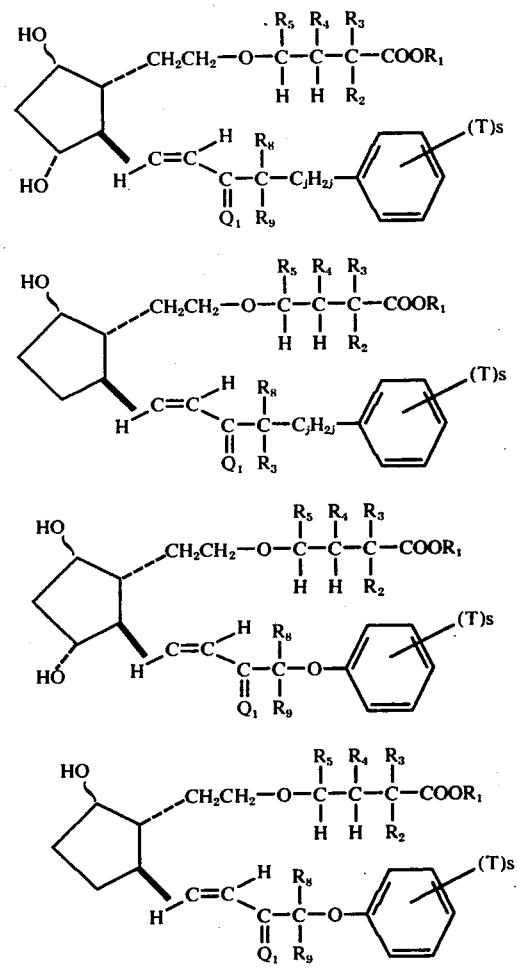

Chart A

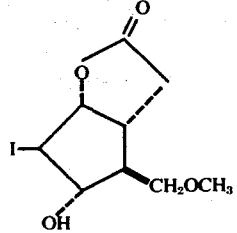

LXIII

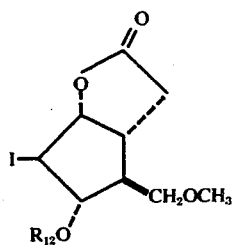

LXIV

Reference to Charts A and B herein will make clear the process steps starting in Chart A with the iodolactone of formula LXIII to provide the lactol of formula LXXII, and in Chart B, the transformation of the more general lactone of formula LXXIII to yield the 5-oxa PGF-type compounds of formula LXXVI.

Chart A-continued
LXV
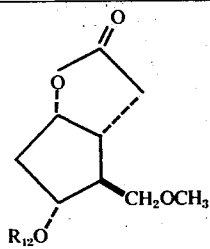
LXVI
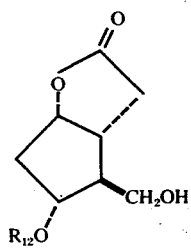
LXVII
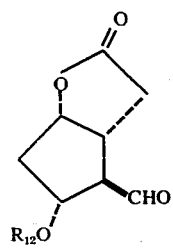
LXVIII
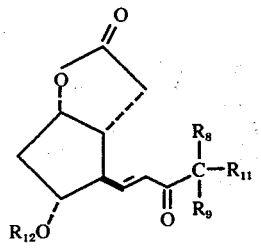
LXIX
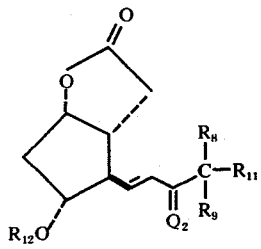
Chart A-continued
LXX
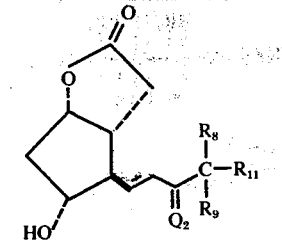
LXXI
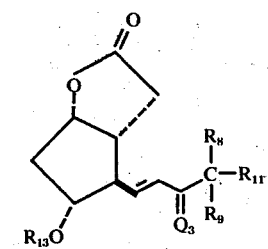
LXXII
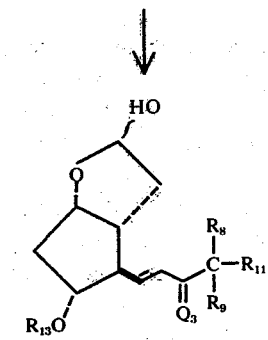
CHART B
LXXIII
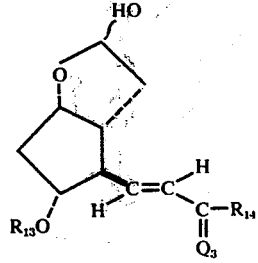
LXXIV
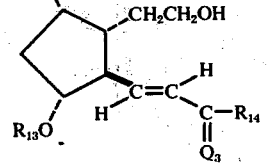

CHART B-continued

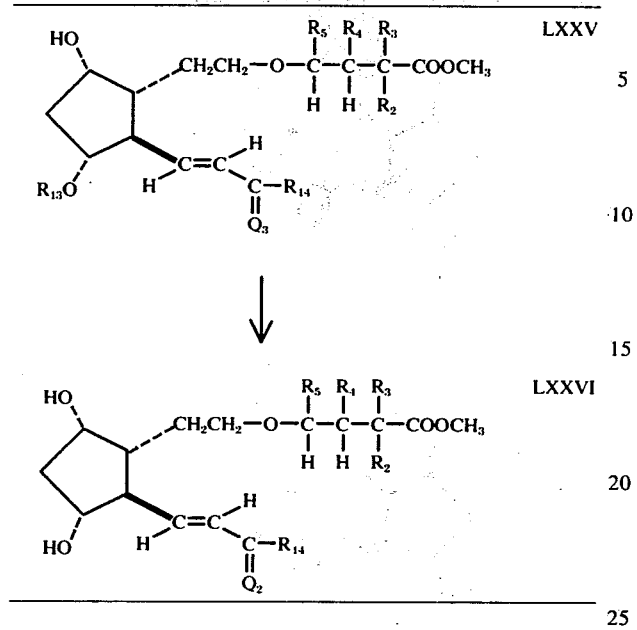

LXXV

LXXVI

Referring to Charts I and J, there is shown a general method for preparing 5-oxa 11-deoxy PGF analogs. In Charts I and J, $R_2$, $R_3$, $R_4$, $R_5R_8$, $R_9$, $R_{11}$, $R_{14}$, $Q_2$, $Q_3$, and ~ have the same meaning ascribed to them above for Charts A and B.

Referring to Chart I, there are shown the steps by which the formula-CII aldehyde is transformed to lactol CVI. Thereafter, product CX is obtained by the steps of Chart J.

CHART I

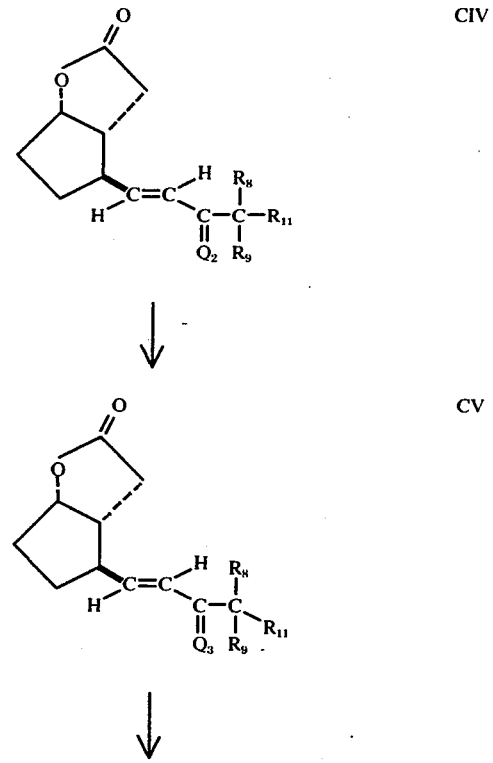

CII

CIII

CHART I-continued

CIV

CV

CVI

CHART J

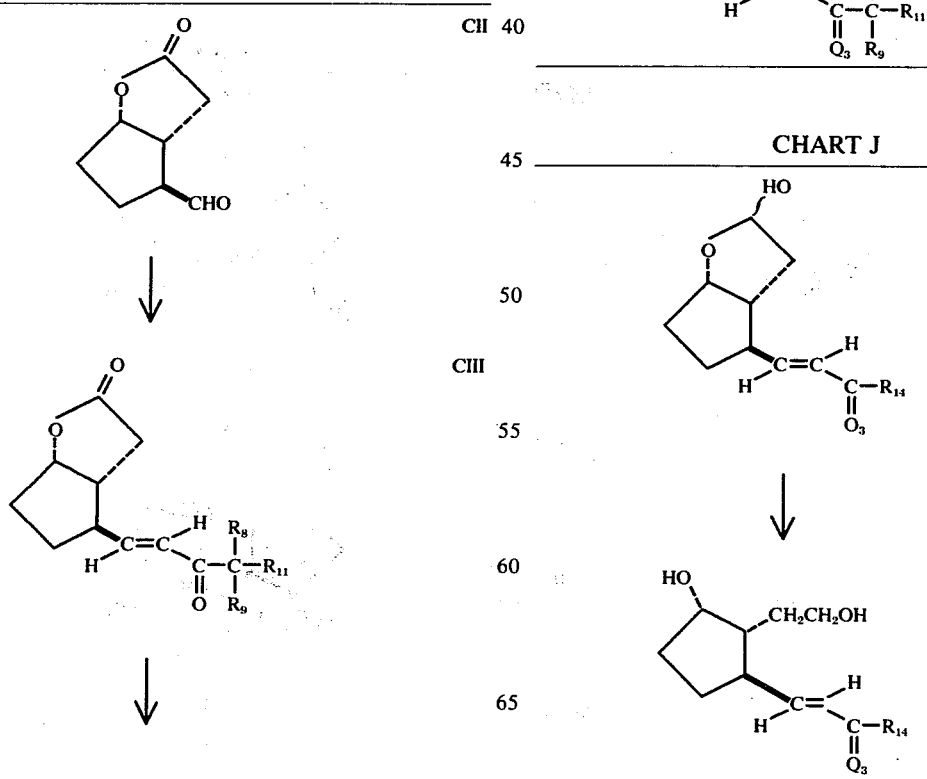

CVII

CVIII

CHART J-continued

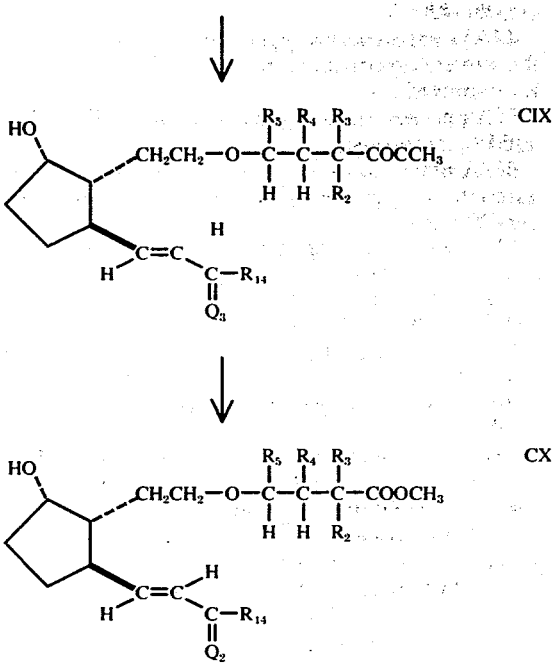

I claim:
1. A process for preparing an optically active compound of the formula

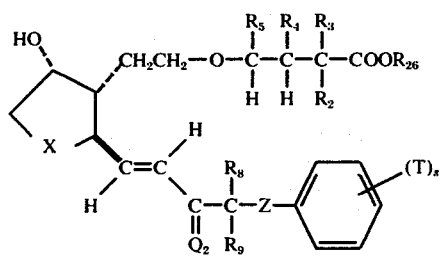

or a racemic compound of that formula and the mirror image thereof, wherein Z represents an oxa atom (—O—) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between —$CR_8R_9$— and the ring; wherein T is alkyl of one to 4 carbon atoms, inclusive, fluoro, chloro, trifluoromethyl, or —$OR_{10}$, wherein $R_{10}$ is hydrogen or alkyl of one to 4 carbon atoms, inclusive, and s is zero, one, 2, or 3, with the proviso that not more than two T's are other than alkyl and when s is 2 or 3 the T's are either the same or different; wherein $Q_2$ is

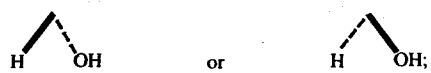

wherein, when Z is oxa (—O—), $R_8$ and $R_9$ are hydrogen or alkyl of 1 to 4 carbon atoms, being the same or different, and, when Z is $C_jH_{2j}$, $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different, with the proviso that no more than one of $R_3$, $R_4$, and $R_5$ is alkyl; and wherein $R_{26}$ is alkyl of one to 3 carbon atoms, inclusive; and wherein X is

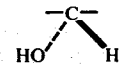

or —$CH_2$—;
which comprises starting with an optically active compound of the formula

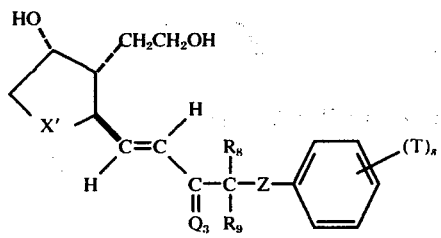

or a racemic compound of that formula and the mirror image thereof, wherein $Q_3$ is

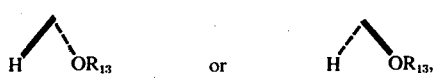

wherein $R_{13}$ is a blocking group, wherein X' is

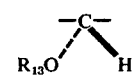

or —$CH_2$—,
and wherein $R_8$, $R_9$, Z, T, and s are as defined above; and subjecting said compound successively to the following reactions:
a. alkylation with an omega-halo ortho ester of the formula

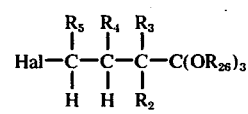

wherein Hal is chloro, bromo, or iodo, and wherein $R_2$, $R_3$, $R_4$, $R_5$ and $R_{26}$ are as defined above, in the presence of a base, with the proviso that, when the base is an organolithium compound, there is present either hexamethylphosphoramide or dimethyl formamide;
b. transformation of the product of step a) to an optically active compound of the formula

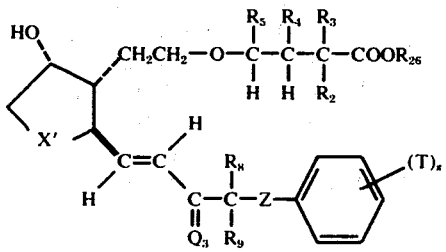

or a racemic compound of that formula and the mirror image thereof, wherein $Q_3$, $R_2$, $R_3$, $R_4$, $R_5$, $R_8$, $R_9$, $R_{13}$, $R_{26}$, s, T, X', and Z are as defined above, by hydrolysis; and c. replacement of the blocking groups with hydrogen, by hydrolysis.

2. A process according to claim 1 wherein $Q_3$ is

wherein $R_{13}$ is a blocking group.

3. A process according to claim 1 wherein the sum of the carbon atoms in $R_8$ and $R_9$ taken together is not greater than 7.

4. A process according to claim 3 wherein $R_3$, $R_4$, and $R_5$ are ether hydrogen or methyl, and one of $R_3$, $R_4$, and $R_5$ is methyl.

5. A process according to claim 3 wherein $R_2$, $R_3$, $R_4$, and $R_5$ are hydrogen.

6. A process according to claim 5 wherein $R_8$ and $R_9$ are either hydrogen or methyl, and at least one of $R_8$ and $R_9$ is methyl.

7. A process according to claim 6 wherein both $R_8$ and $R_9$ are methyl.

8. A process according to claim 5 wherein both $R_8$ and $R_9$ are hydrogen.

9. A process according to claim 8 wherein Z is oxa (—O—).

10. A process according to claim 8 wherein Z is methylene.

11. A process according to claim 1 wherein the condensation of step a) is done in the presence of potassium t-butoxide and tetrahydrofuran.

12. A process according to claim 1 wherein the condensation of step a) is done in the presence of n-butyllithium and hexamethylphosphoramide.

* * * * *